(12) United States Patent
De Boer et al.

(10) Patent No.: US 6,710,006 B2
(45) Date of Patent: Mar. 23, 2004

(54) NON-SYMMETRICAL LIGANDS AND CATALYST SYSTEMS THEREOF FOR ETHYLENE OLIGOMERIZATION TO LINEAR ALPHA OLEFINS

(75) Inventors: Eric Johannes Maria De Boer, Amsterdam (NL); Henderikus Hyacinthus Deuling, Amsterdam (NL); Harry Van Der Heijden, Amsterdam (NL); Nicolaas Meijboom, Amsterdam (NL); Aart Bartus Van Oort, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/775,128

(22) Filed: Feb. 1, 2001

(65) Prior Publication Data

US 2002/0016425 A1 Feb. 7, 2002

(30) Foreign Application Priority Data

Feb. 9, 2000 (EP) .............................................. 00301036

(51) Int. Cl.⁷ .............................. B01J 31/22; C08F 4/44
(52) U.S. Cl. ....................... 502/155; 502/167; 502/168; 526/161; 526/171; 526/172; 556/138
(58) Field of Search .................. 526/161, 171, 526/172; 502/155, 167, 168; 556/138

(56) References Cited

U.S. PATENT DOCUMENTS

| | | | |
|---|---|---|---|
| 5,955,555 A | 9/1999 | Bennett | 526/133 |
| 6,063,881 A | * 5/2000 | Bennett | 526/161 |
| 6,103,946 A | 8/2000 | Brookhart, III et al. | 585/523 |
| 6,150,482 A | 11/2000 | Brookhart et al. | 526/161 |

FOREIGN PATENT DOCUMENTS

| | | | |
|---|---|---|---|
| WO | WO 98/27124 | 6/1998 | C08F/10/00 |
| WO | WO 99/02472 | 1/1999 | C07C/2/32 |

OTHER PUBLICATIONS

"Oligomerization of Ethylene to Higher Linear α–Olefins," by Dieter Vogt, *Applied Homogeneous Catalysis With Organometallic Compounds*, Ed. B. Bornilis, W. A. Herrmann, vol. 1, Ch. 2.3.1.3, (1996) pp. 245–258.

"Novel, Highly Active Iron and Cobalt Catalysts for Olefin Polymerization," by Alison M. A. Bennett, Chemtech, Jul. 1999, pp. 24–28.

"Iron–Based Catalysts With Exceptionally High Activities and Selectives for Oligomerization of Ethylene to Linear α–Olefins," Brooke L. Small and Maurice Brookhart, *J. Am. Chem. Soc.*1998, 120, pp. 7143–7144.

"Polymerization of Propylene by a New Generation of Iron Catalysts: Mechanisms of Chain Initiation, Propagation, and Termination," by Brooke L. Small and Maurice Brookhart, Macromolecules, vol. 32, No. 7, 1999, pp. 2120–2130.

* cited by examiner

*Primary Examiner*—Robert Harlan

(57) ABSTRACT

Non-symmetrical ligands of formula (I);

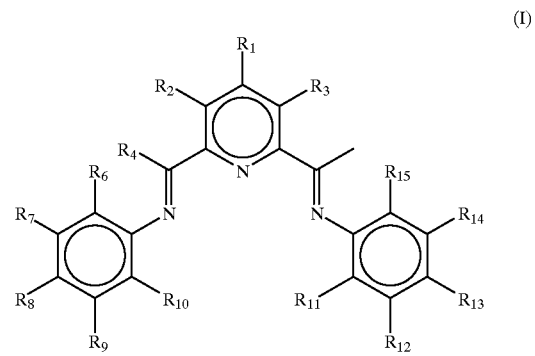

bis-aryliminepyridine $MX_n$ complexes comprising a non-symmetrical ligand of formula (I), wherein M is a metal selected from Fe or Co, n is 2 or 3, and X is halide, optionally substituted hydrocarbyl, alkoxide, amide, or hydride; [bis-aryliminepyridine $MY_p \cdot L_n^+][NC^-]_q$ complexes, comprising a non-symmetrical ligand of formula (I), wherein Y is a ligand which may insert an olefin, M is Fe or Co, $NC^-$ is a non-coordinating anion and p+q is 2 or 3, matching the formal oxidation of the metal atom M, L is a neutral Lewis donor molecule and n=0, 1, or 2; and processes for the production of alpha-olefins from ethylene, using said complexes.

91 Claims, 3 Drawing Sheets

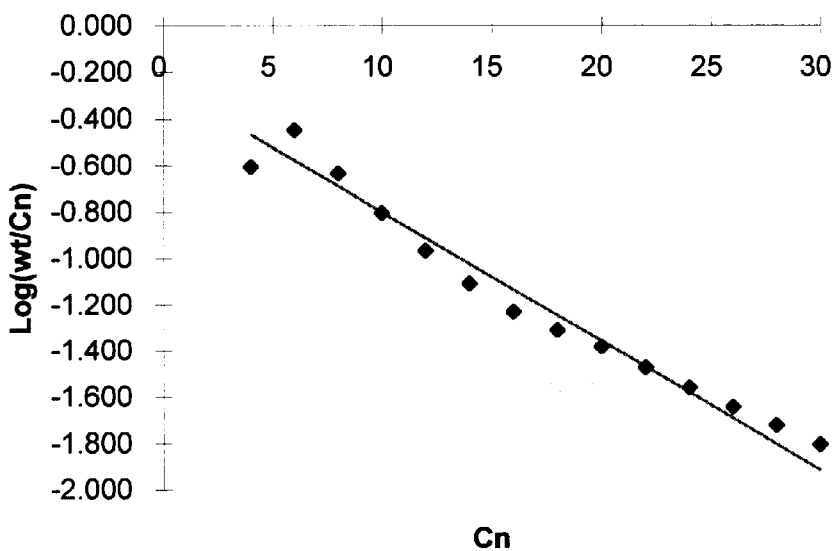
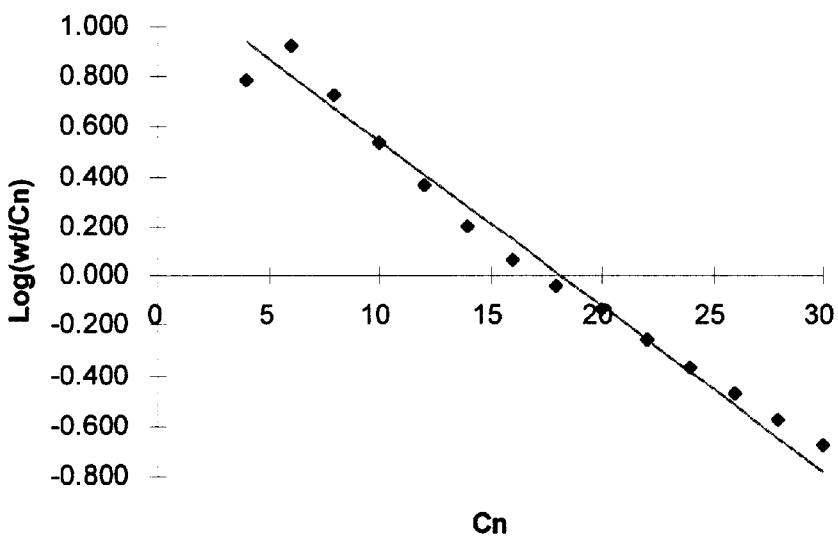

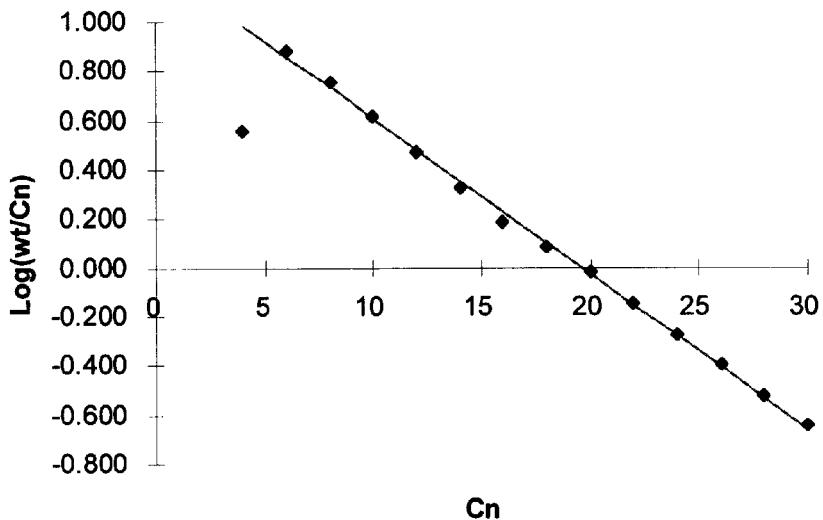
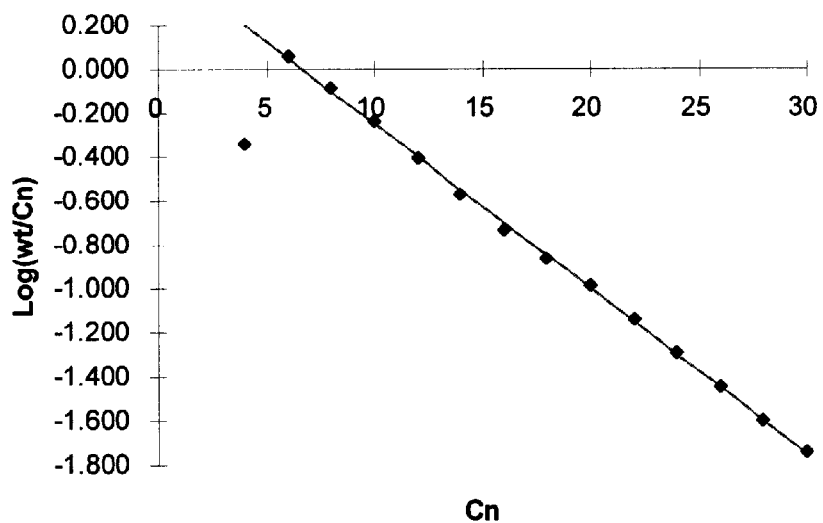

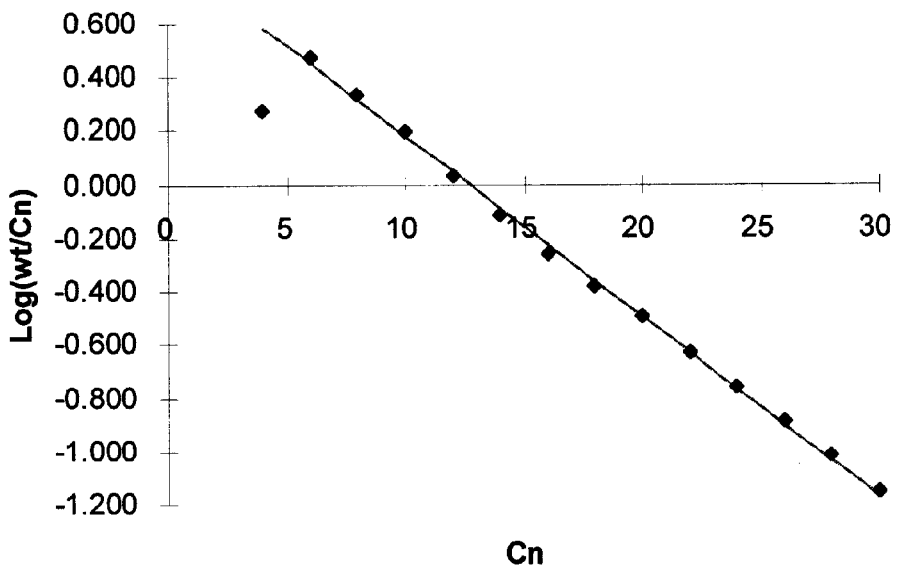
Figure 5: Regression Analysis of Experiment 5
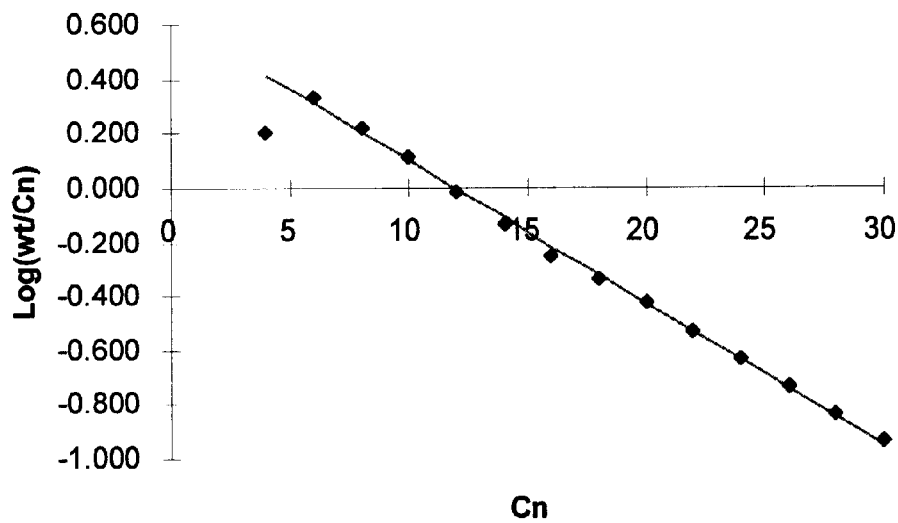
Figure 6: Regression Analysis of Experiment 6

NON-SYMMETRICAL LIGANDS AND CATALYST SYSTEMS THEREOF FOR ETHYLENE OLIGOMERIZATION TO LINEAR ALPHA OLEFINS

The present invention relates to non-symmetrical ligands, various non-symmetrical catalyst precursors and catalyst systems derived from these ligands for ethylene oligomerisation to linear alpha olefins in high yield and very high selectivity, and a process for preparing said linear alpha olefins.

BACKGROUND OF THE INVENTION

Various processes are known for the production of higher linear alpha olefins (for example D. Vogt, *Oligomerisation of ethylene to higher α-olefins in Applied Homogeneous Catalysis with organometallic Compounds* Ed. B. Cornils, W. A. Herrmann Vol. 1, Ch. 2.3.1.3, page 245, VCH 1996). These commercial processes afford either a Poisson or Schulz-Flory oligomer product distribution. In order to obtain a Poisson distribution, no chain termination must take place during oligomerisation. However, in contrast, in a Schulz-Flory process, chain termination does occur and is independent from chain length. The Ni-catalysed ethylene oligomerisation step of the Shell Higher Olefins Process (SHOP) is a typical example of a Schulz-Flory process.

In a Schulz-Flory process, a wide range of oligomers are typically made in which the fraction of each olefin can be determined by calculation on the basis of the so-called K-factor. The K-factor, which is indicative of the relative proportions of the product olefins, is the molar ratio of $[C_{n+2}]/[C_n]$ calculated from the slope of the graph of log $[C_n$ mol %] versus n, where n is the number of carbon atoms in a particular product olefin.

The K-factor is by definition the same for each n. By ligand variation and adjustment of reaction parameters, the K-factor can be adjusted to higher or lower values. In this way, the process can be operated to produce a product slate with an optimised economic benefit. When demand for the $C_6$–$C_{18}$ fraction is much higher than for the $C_{>20}$ fraction, processes are geared to produce the lower carbon number olefins. However, the formation of the higher carbon number olefins is inevitable, and, without further processing, the formation of these products can be detrimental to the profitability of the process. To reduce the negative impact of the higher carbon number olefins and of the low value $C_4$ fraction in such processes, additional technology has been developed to reprocess these streams and convert them into more valuable chemicals such as internal $C_6$–$C_{18}$ olefins. However, this technology is expensive both from an investment and operational point of view and consequently adds additional cost. Therefore, considerable effort is directed to keep the production of the higher carbon numbered olefins to the absolute minimum, i.e. not more than inherently associated with the Schulz-Flory K-factor.

In WO-A-99/02472 novel Fe-based ethylene oligomerisation catalysts are described that show high activity and high selectivity towards linear alpha olefins. The catalysts are based on iron complexes of a selected 2,6-pyridinedicarboxaldehyde bisimine or a selected 2,6-diacylpyridine bisimine. In the present invention the term "bis-(aryliminoalkyl)pyridine", or in short, "bis-aryliminepyridine" is used to describe both classes of ligands. In WO-A-99/02472, the oligomer product distribution made with these catalysts is not specified any further, but is implied to be Schulz-Flory in view of the definition, the use, and the determination of the Schulz-Flory K-factor. In other publications, such as A. M. A. Bennett *Chemtech* July 1999, page 24–28; and references mentioned therein, the product composition was stated to obey a Schulz-Flory distribution. The accompanying experimental data in WO-A-99/02472, however, shows that these catalysts afford a product slate with a surprisingly large amount of heavy products. It has been confirmed that the disclosed oligomerisation catalysts afford a product composition which, in comparison with a Schulz-Flory distribution, contains indeed significantly more heavy products than expected.

Indeed, Table 1 on page 30 of WO-A-99/02472 gives an overview of ethylene oligomerisation experiments catalysed by four different iron complexes (X–XIII). Experiment numbers 16 and 17 of this Table, in which iron complex XI is being used at ethylene pressure of 1.4 MPa (gauge) or 1.5 MPa (15 bar(a)) and 2.8 MPa (gauge) or 2.9 MPa (29 bar(a)) respectively, both give rise to a Schulz-Flory K-factor of 0.79, as derived from the $C_{16}/C_{14}$ ratio. If it is assumed that a perfect Schulz-Flory distribution is obtained in these experiments, i.e. $C_{n+2}/C_n$=K=0.79, it can be calculated that the $C_{30}$–$C_{100}$ fraction is 15% wt and the $C_{20}$–$C_{28}$ fraction is 21% wt on total product. If it is further assumed that the solids mentioned in Table 1 contain the $C_{20}$–$C_{100}$ fraction then this should amount to 36% wt on total product. This should be considered as a maximum solids content since at least the major part of the lowest ethylene oligomers in this fraction remain dissolved in the toluene-solution of the $C_4$–$C_{18}$ fraction. In Experiment numbers 16 and 17 of Table 1, however, the amount of solids isolated are 14.1 g and 18.0 g, which may be calculated as a solids content of 45% wt and 58% wt on total product, respectively.

Similarly, for a K-factor of 0.81 it can be calculated that the $C_{20}$–$C_{28}$ fraction and the $C_{30}$–$C_{100}$ fraction are 22% wt and 20% wt on total product, respectively, or maximally 42% wt for the solids content. For Experiment number 18 in Table 1, also using iron complex XI, but now at pressure of 0 MPa (gauge), i.e. 0.1 MPa (1 bar(a)), the amounts of solids isolated are 2.7 g , which may be calculated as a solids content of 54% wt on total product.

The distributions obtained in Experiment numbers 16–18 in Table 1 of WO-A-99/02472 clearly indicate that larger quantities of higher carbon number products, i.e. solids (>$C_{20}$), are produced than would be expected on the basis of the Schulz-Flory K-factor.

SUMMARY OF THE INVENTION

A non-symmetrical bis-aryliminepyridine ligand useful in a catalyst system is provided having a formula (I),

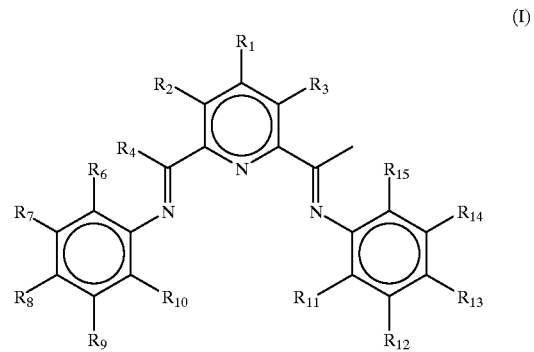

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, and $R_{11}$, and $R_{15}$ are, independently, hydrogen or an inert functional group.

The present invention further provides a bis-aryliminepyridine $MX_n$ complex comprising a non-symmetrical ligand of formula (I) and wherein M is a metal atom selected from Fe or Co, n is 2 or 3, and X is halide, optionally substituted hydrocarbyl, alkoxide, amide, or hydride and a process for the production of alpha-olefins by contacting one or more such complexes with ethylene and a second compound which is capable of transferring an optionally substituted hydrocarbyl or hydride group to a metal atom M, and which is also capable of abstracting an $X^-$ group from such metal atom.

The present invention further provides a [bis-aryliminepyridine $MY_p.L_n^+$][$NC^-$]$_q$ complex comprising a non-symmetrical ligand of formula (I) and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2 and a process for the production of alpha-olefins by contacting one or more such complexes with ethylene.

BRIEF DESCRIPTION OF THE DRAWING

FIG. 1 is a regression analysis of Comparative Example A.

FIG. 2 is a regression analysis of Comparative Example C.

FIG. 3 is a regression analysis of Experiment 1.

FIG. 4 is a regression analysis of Experiment 4.

FIG. 5 is a regression analysis of Experiment 5.

FIG. 6 is a regression analysis of Experiment 6.

DETAILED DESCRIPTION OF THE INVENTION

In view of the negative effect of excess of heavy ends on the economics of the technology, we have further explored such systems to improve the product distribution, and have now surprisingly found new catalyst systems which not only afford a Schulz-Flory product distribution, but which also show an improved selectivity and activity over the previously disclosed catalysts.

The present invention provides a non-symmetrical bis-aryliminepyridine ligand of formula (I), wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, and $R_{11}$, and $R_{15}$ are, independently, hydrogen or an inert functional group.

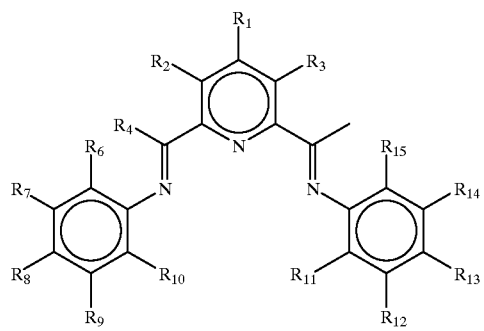

(I)

The present invention further provides a bis-aryliminepyridine $MX_n$ complex comprising a non-symmetrical ligand of formula (I), wherein M is a metal atom selected from Fe or Co, n is 2 or 3, and X is halide, optionally substituted hydrocarbyl, alkoxide, amide, or hydride.

In a further aspect, the present invention provides a process for the production of alpha-olefins, which comprises contacting one or more $MX_n$ complexes of the present invention with ethylene and a second compound which is capable of transferring an optionally substituted hydrocarbyl or hydride group to a metal atom M selected from Fe or Co, and which is also capable of abstracting an $X^-$ group from said metal atom, at a temperature in the range of about –100° C. to about +300° C.

In a still further aspect, the present invention provides a process for the production of alpha-olefins, which comprises contacting one or more $MX_n$ complexes of the present invention with ethylene and a second compound which is capable of transferring an optionally substituted hydrocarbyl or hydride group to a metal atom M selected from Fe or Co, and a third compound which is capable of abstracting an $X^-$ group from said metal atom, at a temperature in the range of about –100° C. to about +300° C.

The present invention further provides a [bis-aryliminepyridine $MY_p.L_n^+$][$NC^-$]$_q$ complex comprising a non-symmetrical ligand of formula (I), wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

The present invention further provides a process for the production of alpha-olefins, comprising contacting one or more [bis-aryliminepyridine $MY_p.L_n^+$][$NC^-$]$_q$ complexes of the present invention with ethylene at a temperature in the range of about –100° C. to about +300° C.

In the present invention certain terms are used as follows:

The term "non-symmetrical" is used in relation to the four ortho-positions of the two aryl-imino groups and defines these as such that neither the substitution pattern nor the substituents themselves afford two equally ortho-substituted aryl-imino groups.

Hydrocarbyl group: a group containing only carbon and hydrogen. Unless otherwise stated, the number of carbon atoms is preferably between 1 and 30.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the oligomerisation process. Non-limiting examples of such inert groups are fluoride, chloride, silanes, stannanes, ethers and amines with adequate steric shielding, all well-known to those skilled in the art.

Inert functional group: a group other than optionally substituted hydrocarbyl which is inert under the process conditions. By "inert" is meant that the functional group does not interfere to any substantial degree with the oligomerisation process. Examples of inert functional groups include halide, ethers, silanes, siloxanes, and amines, in particular tertiary amines.

Primary carbon atom group: a —$CH_2$—R group wherein R may be hydrogen, optionally substituted hydrocarbyl, inert functional group. Examples of primary carbon atom groups include —$CH_3$, —$C_2H_5$, —$CH_2Cl$, —$CH_2OCH_3$, —$CH_2N(C_2H_5)_2$, —$CH_2Ph$.

Secondary carbon atom group: a —CH—$R_2$ group wherein R may be optionally substituted hydrocarbyl, inert functional group. Examples of secondary carbon atom groups include —$CH(CH_3)_2$, —$CHCl_2$, —$CHPh_2$, —CH=$CH_2$, cyclohexyl.

Tertiary carbon atom group: a —C—$R_3$ group wherein R may be optionally substituted hydrocarbyl, inert functional group. Examples of tertiary carbon atom groups include —$C(CH_3)_3$, —$CCl_3$, —C≡-CPh, 1-Adamantyl, —$C(CH_3)_2$($OCH_3$).

By a "ligand which may insert an olefin" is meant a ligand which is coordinated to a metal ion into which bond an ethylene molecule may be inserted to initiate or propagate an oligomerisation reaction. In [bis-aryliminepyridine $MY_p.L_n^+$][$NC^-$]$_q$ complexes according to the present invention, Y may be hydride, alkyl or any other anionic ligand which may insert an olefin.

By "non-coordinating anion" is meant an anion which does not substantially coordinate to the metal atom M. Non-coordinating anions (NC-) that may be suitably employed include bulky anions such as tetrakis [3,5-bis(trifluoromethyl)phenyl]borate ($BAF^-$), ($C_6F_5$)$_4B^-$, and anions of alkylaluminium compounds including $R_3AlX^-$, $R_2AlClX^-$, $RAlCl_2X^-$, and "$RAlOX^-$", wherein R is hydrogen, optionally substituted hydrocarbyl or an inert functional group, and X is halide, alkoxide or oxygen.

It will be appreciated by those skilled in the art that within the boundary conditions herein before described, substituents $R_1$–$R_{15}$ may be readily selected to optimize the performance of the catalyst system and its economical application.

The present invention provides non-symmetrical bis-aryliminepyridine ligands of formula (I) wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring; and a) $R_6$ is an inert functional group or an optionally substituted hydrocarbyl, and $R_{10}$, $R_{11}$, and $R_{15}$ are, independently, hydrogen or halide; or b) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or c) $R_6$ is taken together with $R_7$ to form a ring, $R_{10}$ is a primary carbon atom group, an inert functional group, or hydrogen and $R_{11}$ and $R_{15}$ are, independently, hydrogen or halide; or d) $R_6$ and $R_{10}$ are taken together with $R_7$ and $R_9$ respectively to form rings and $R_{11}$ and $R_{15}$ are, independently, hydrogen or halide;

Substituents $R_1$–$R_{15}$ may independently be linked together and form cyclic structures. Examples of such structures include the linking of, for example, $R_6$ with $R_7$, to form the basic naphthyl skeleton or a tetrahydronaphthyl unit.

Furthermore it will be readily appreciated by any person who has mastered the basic principles of homogeneous catalysis that substituent variations of $R_1$–$R_5$, $R_7$–$R_9$, and $R_{12}$–$R_{14}$ may be selected so as to enhance other desirable properties of catalyst precursors and catalyst systems such as solubility in non-polar solvents or extending the range of suitable starting materials in their syntheses.

Preferred embodiments of this invention are ligands according to (I) and derivatives thereof, in which the following R groups appear:

$R_1$–$R_3$ are hydrogen; and/or $R_4$ and $R_5$ are methyl, hydrogen or phenyl, preferably methyl; and/or combinations of ortho-substituents in which $R_6$ is methyl, ethyl, iso-propyl, phenyl, tertiary-butyl, or linked to $R_7$ to form a naphthyl skeleton, preferably iso-propyl or tertiary-butyl; $R_{10}$, $R_{11}$, and $R_{15}$ are, independently, hydrogen, fluoride, or chloride; and/or combinations of ortho-substituents in which $R_6$ and $R_{10}$ are, independently, methyl, ethyl, or linked to $R_7$ and $R_9$ respectively to form an anthracene skeleton, preferably methyl; $R_{11}$ and $R_{15}$ are, independently, hydrogen, fluoride or chloride.

It is particularly preferred that $R_{11}$ and $R_{15}$ are, independently, hydrogen or fluoride.

In a preferred embodiment, a non-symmetrical ligand of formula (I) is provided, wherein $R_1$–$R_3$ are hydrogen; $R_4$, $R_5$, $R_6$, $R_8$ and $R_{10}$ are methyl; $R_7$, $R_9$, $R_{11}$, $R_{12}$, $R_{14}$ and $R_{15}$ are hydrogen; and $R_{13}$ is tertiary-butyl.

Another preferred embodiment provides a non-symmetrical ligand of formula (I), wherein $R_{1-3}$ are hydrogen; $R_4$, $R_5$, $R_6$, $R_8$ and $R_{10}$ are methyl; $R_7$, $R_9$, $R_{11}$, $R_{12}$, $R_{14}$ and $R_{15}$ are hydrogen; and $R_{13}$ is methoxy.

Yet another preferred embodiment provides a non-symmetrical ligand of formula (I), wherein $R_{1-3}$ are hydrogen; $R_4$, $R_5$, $R_6$, $R_8$ and $R_{10}$ are methyl; $R_7$, $R_9$, $R_{11}$, $R_{12}$, $R_{14}$ and $R_{15}$ are hydrogen; and $R_{13}$ is trimethylsiloxy.

In another preferred embodiment, a non-symmetrical ligand of formula (I) is provided, wherein $R_1$–$R_3$ are hydrogen; $R_4$, $R_5$, $R_6$, $R_8$ and $R_{10}$ are methyl; $R_7$, $R_9$, $R_{12}$, $R_{13}$, $R_{14}$ and $R_{15}$ are hydrogen; and $R_{11}$ is fluoride.

In the derived bis-aryliminepyridine $MX_n$ complex, X may conveniently be halide, preferably, chloride.

In a preferred embodiment of the bis-aryliminepyridine $MX_n$ complex, metal atom M is Fe and n is 2. In another preferred embodiment, metal atom M is Fe and n is 3.

Compounds which are capable of transferring an optionally substituted hydrocarbyl or hydride group to metal atom M, and which are also capable of abstracting an $X^-$ group from metal atom M include alkylaluminium compounds such as alkylaluminoxane and alkylaluminium halides. A preferred compound is methylaluminoxane.

Compounds which are capable of transferring an optionally substituted hydrocarbyl or hydride group to metal atom M include alkylaluminium compounds including alkyl aluminoxanes, alkyl lithium compounds, Grignards, alkyl tin and alkyl zinc compounds.

Compounds which are capable of abstracting an X⁻ group from metal atom M include strong neutral Lewis acids such as $SbF_5$, $BF_3$ and $Ar_3B$, wherein Ar is a strong electron-withdrawing aryl group such as $C_6F_5$ or $3,5-(CF_3)_2C_6H_3$.

A neutral Lewis donor molecule is a compound which may suitably act as a Lewis base, such as ethers, amines, sulphides and organic nitrites.

In the [bis-aryliminepyridine $MY_p.L_n^+$][$NC^-$]$_q$ complex according to the present invention, L may be a neutral Lewis donor molecule capable of being displaced by ethylene, or a vacant coordination site.

In the [bis-aryliminepyridine $MY_p.L_n^+$][$NC^-$]$_q$ complex according to the present invention, metal atom M is preferably Fe and the formal oxidation state of said metal atom may be 2 or 3.

The catalyst system may be formed by mixing together the complex and optional additional compounds, preferably in a solvent such as toluene or isooctane.

The mole ratio of the complex, second compound, and optionally third compound is not limited in the present invention.

Such a quantity of the catalyst system is usually employed in the oligomerisation reaction mixture so as to contain from $10^{-4}$ to $10^{-9}$ gram atom, more preferably $10^{-6}$ to $10^{-7}$ gram atom, of metal atom M, in particular of Fe [II] or [III] metal per mole of ethylene to be reacted.

The oligomerisation reaction may be most conveniently conducted over a range of temperatures from about –100° C. to about +300° C., preferably in the range of from about 0° C. to about 200° C., and more preferably in the range of from about 50° C. to about 150° C.

The oligomerisation reaction may be conveniently carried out at a pressure of about 0.01 to about 15 MPa (about 0.1 to about 150 bar(a)), more preferably about 1 to about 10 MPa (about 10 to about 100 bar(a)), and most preferably about 1.5 to about 5 MPa (about 15 to about 50 bar(a)).

The optimum conditions of temperature and pressure used for a particular catalyst system to maximise the yield of oligomer, and to minimise the competing reactions such as dimerisation and polymerisation can be readily established by one skilled in the art.

The conditions of temperature and pressure are preferably selected to yield a product slate with a K-factor within the range of from 0.50 to 0.90, preferably in the range of from 0.65 to 0.85 and most preferably in the range of from 0.70 to 0.80. In the present invention, polymerisation is deemed to have occurred when a product slate has a K-factor greater than 0.9.

The oligomerisation reaction can be carried out in the gas phase or liquid phase, or mixed gas-liquid phase, depending upon the volatility of the feed and product olefins.

The oligomerisation reaction is carried out in the presence of an inert solvent which may also be the carrier for the catalyst and/or feed olefin. Suitable solvents include alkanes, alkenes, cycloalkanes, and aromatic hydrocarbons. For example, solvents that may be suitably used according to the present invention include hexane, isooctane, benzene, toluene, and xylene.

Reaction times of from about 0.1 to about 10 hours have been found to be suitable, dependent on the activity of the catalyst. The reaction is preferably carried out in the absence of air or moisture.

The oligomerisation reaction may be carried out in a conventional fashion. It may be carried out in a stirred tank reactor, wherein olefin and catalyst or catalyst precursors are added continuously to a stirred tank and reactant, product, catalyst, and unused reactant are removed from the stirred tank with the product separated and the catalyst and unused reactant recycled back to the stirred tank.

Alternatively, the reaction may be carried out in a batch reactor, wherein the catalyst precursors, and reactant olefin are charged to an autoclave, and after being reacted for an appropriate time, product is separated from the reaction mixture by conventional means, such as distillation.

After a suitable reaction time, the oligomerisation reaction can be terminated by rapid venting of the ethylene in order to deactivate the catalyst system.

The resulting alpha olefins have a chain length of from 4 to 100 carbon atoms, preferably 4 to 30 carbon atoms, and most preferably from 4 to 20 carbon atoms.

Product olefins can be recovered suitably by distillation and further separated as desired by distillation techniques dependent on the intended end use of the olefins.

The present invention is illustrated by the following Examples, which should not be regarded as limiting the scope of the invention in any way.

General Procedures and Characterisation

All the operations with the catalyst systems were carried out under nitrogen atmosphere.

Isooctane (2,4,4-trimethylpentane, 99.8% purity) (ex. Merck) was dried by prolonged nitrogen purge, followed by passage over 4 Å molecular sieves (final water content of about 1 ppm).

Anhydrous toluene (99.8% purity) (ex. Aldrich) was dried over 4 Å molecular sieves (final water content of about 3 ppm).

Ethylene (99.5% purity) was purified over a column containing 4 Å molecular sieves and BTS catalyst (ex. BASF) in order to reduce water and oxygen content to <1 ppm.

4-Methoxyaniline, 4-hydroxyaniline, hexamethyldisilazane and trimethylchlorosilane are available from Aldrich.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. Response factors for the even linear α-olefins and for cis- and trans-2-hexene, relative to n-hexylbenzene (internal standard) were determined using a standard calibration mixture. The yields of the $C_4$–$C_{30}$ olefins were obtained from the GC analysis, from which the K-factor and the theoretical yield of $C_4$–$C_{100}$ olefins, i.e. total oligomerisation product (Total Product), were determined by regression analysis, using the $C_6$–$C_{28}$ data.

The relative amounts of the linear 1-hexene amongst all hexene isomers and the relative amount of 1-dodecene amongst all dodecene isomers found from the GC analysis is used as a measure of the selectivity of the catalyst towards linear a-olefin formation.

By turnover frequency (T.O.F) is meant the number of moles of ethylene oligomerised per hour per mole of iron compound.

The NMR data were obtained at room temperature with a Varian 300 and 400 MHz apparatus.

Catalyst Components

1. Preparation of 2,6-bis-[1-(2-methylphenylimino)ethyl] pyridine iron[II] chloride complex (X) X was prepared according to the method disclosed in WO-A-99/02472.
2. Preparation of 2,6-bis-[1-(2-ethylphenylimino)ethyl] pyridine iron[II] chloride complex (XI) XI was prepared according to the method disclosed in WO-A-99/02472.
3. Preparation of 2-[1-(2,4,6-trimethylphenylimino)ethyl]-6-acetylpyridine (1)

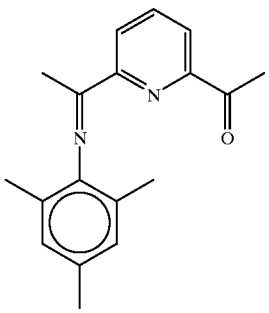

(1)

2,6-Diacetylpyridine (7.3 g, 44.8 mmol) (ex. Aldrich) and 2,4,6-trimethylaniline (5.74 g, 42.55 mmol) (ex. Aldrich) were dissolved in 450 ml of toluene. To this solution, 4 Å molecular sieves and a small amount of p-toluenesulphonic acid (0.22 mmol) (ex. Aldrich) were added. The mixture was refluxed for 16h. After filtration the solvent was removed in vacuo. Several crystallisations from ethanol yielded 3.42 g (28.7%) of monoimine (1). $^1$H-NMR (CDCl$_3$) δ 8.55 (d, 1H, Py-H$_m$), 8.11 (d, 1H, Py-H$_m$), 7.92 (t, 1H, Py-H$_p$), 6.89 (s, 2H, ArH), 2.77 (s, 3H, Me), 2.27 (s, 3H, Me), 2.22 (s, 3H, Me), 1.99 (s, 6H, Me).

4. 4. Preparation of 2-[1-(2,4,6-trimethylphenylimino)ethyl]-6-[1-(4-tert-butylphenylimino)ethyl]pyridine (2)

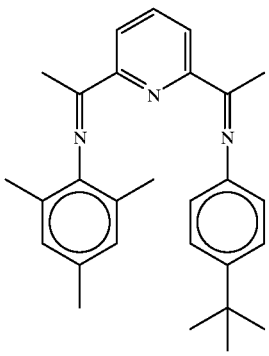

(2)

Monoimine (1, 2.8 g, 10 mmol) and 4-tert-butylaniline (1.49 g, 10 mmol) (ex. Aldrich) were dissolved in 100 ml of toluene. To this solution, 4 Å molecular sieves and a small amount of p-toluenesulphonic acid (0.1 mmol) (ex. Aldrich) were added. After standing for 5 days with addition of more 4 Å molecular sieves, the mixture was refluxed for 2 h. After filtration the solvent was removed in vacuo. The residue was washed with methanol and recrystallised from ethanol. Yield 2.4 g (58%) of mixed diimine (2). $^1$H-NMR (CDCl$_3$) δ 8.42 (d, 1H, Py-H$_m$), 8.34 (d, 1H, Py-H$_m$), 7.86 (t, 1H, Py-H$_p$) 7.38 (d, 2H, ArH), 6.89 (s, 2H, ArH), 6.78 (d, 2H, ArH), 2.42 (s, 3H, Me), 2.29 (s, 3H, Me), 2.22 (s, 3H, Me), 2.00 (s, GH, Me), 1.34 (s, 9H, Bu$^t$).

5. Preparation of 2-[1-(2,4,6-trimethylphenylimino)ethyl]-6-[1-(4-tert-butylphenylimino)ethyl] pyridine iron[II] chloride complex, (3)

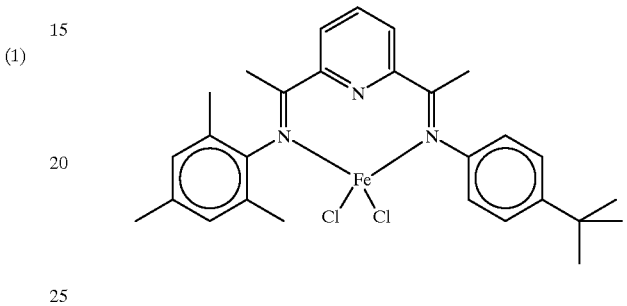

(3)

In an inert atmosphere a solution of 1.5 g diimine (2, 3.6 mmol) in 100 ml dichloromethane (ex. Aldrich) was added to 420 mg FeCl$_2$ (3.3 mmol) (ex. Aldrich) in 150 ml dichloromethane. The mixture was stirred for one week. The developed blue precipitate was isolated by filtration and dried in vacuo. Yield 1.5 g (84w) of iron complex (3). $^1$H-NMR (Cl$_2$CDCDCl$_2$, broad signals) δ 79.3 (1H, Py-H$_m$), 77.7 (1H, Py-H$_m$), 27.0 (1H, Py-H$_p$), 20.7 (3H, Me), 17.3 (6H, Me), 15.0 (2H, ArH), 14.3 (2H, ArH), 1.2 (9H, Bu$^t$), −2.6 (3H, MeC═N), −17.9 (2H, o-ArH), −32.1 (3H, MeC═N).

6. Preparation of 2-[1-(2,4,6-trimethylphenylimino)ethyl]-6-[1-(2-fluorophenylimino)ethyl]pyridine, (4)

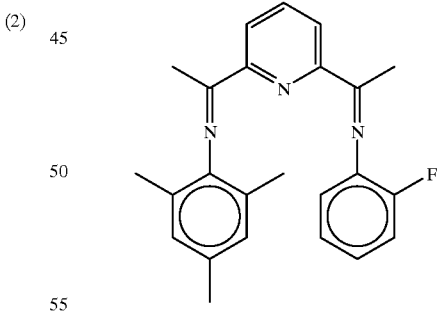

(4)

Monoimine (1, 1.0 g, 3.57 mmol) and 2-fluoroaniline (398 mg, 3.57 mmol) (ex. Aldrich) were dissolved in 50 ml of toluene. To this solution, 4 Å molecular sieves were added. After standing for 20 hrs., with addition of more molecular sieves, the mixture was filtered. The solvent was removed in vacuum and the oily residue was warmed in ethanol (50° C.). The yellow solid, which precipitated after cooling at −20° C., was filtered off and dried in vacuo. Yield 300 mg (23%) of mixed diimine (4).

$^1$H-NMR (CDCl$_3$) δ 8.45 (d, 1H, Py-H$_m$), 8.38 (d, 1H, Py-H$_m$), 7.88 (t, 1H, Py-H$_p$), 7.1 (m, 4H, ArH), 6.93 (dd, 2H, ArH), 6.89 (s, 2H, ArH), 2.41 (s, 3H, Me), 2.29 (s, 3H, Me), 2.22 (s, 3H, Me), 2.00 (s, 6H, Me). $^{19}$F-NMR (CDCl$_3$) δ −126.8

7. Preparation of 2-[1-(2,4,6-trimethylphenylimino)ethyl]-6-[1-(2-fluorophenylimino)ethyl]pyridine iron[II] chloride complex, (5)

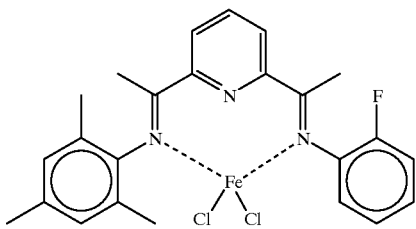

(5)

In an inert atmosphere a solution of 270 mg diimine (4, 0.72 mmol) in 5 ml dichloromethane (ex. Aldrich) was added to 87 mg FeCl$_2$ (0.67 mmol) (ex. Aldrich) in 20 ml dichloromethane. The mixture was stirred for 20 hours. Addition of 10 ml pentane yielded a blue precipitate, which was isolated by centrifugation and dried in vacuo. Yield 175 mg (51%) of iron complex (5).

$^1$H-NMR (CD$_2$Cl$_2$, broad signals, selective data) δ 84.5 (1H, Py-H$_m$), 80.4 (1H, Py-H$_m$), 21.2 (1H, Py-H$_p$), 4.5 (3H, MeC=N), −24.5 (1H, o-ArH), −38.1 (3H, MeC=N). $^{19}$F-NMR (CD$_2$Cl$_2$) δ −95.0

8. Preparation of 2-[1-(2,4,6-trimethylphenylimino)ethyl]-6-[1-(4-methoxyphenylimino)ethyl]pyridine (6)

(6)

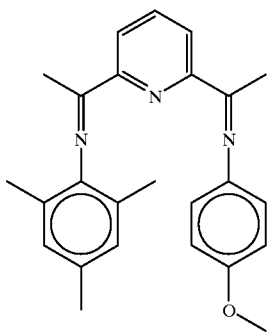

Monoimine (1, 280 mg, 1 mmol) and 4-methoxyaniline (123 mg, 1 mmol) were dissolved in 20 ml of toluene. To this solution 4 Å molecular sieves were added. After standing for 6 days at room temperature the reaction mixture was filtered and the solvent was removed in vacuo. The residue was recrystallised from ethanol. Yield 148 mg (38%) of mixed diimine (6). $^1$H-NMR (CDCl$_3$) δ 8.42 (dd, 1H), 8.34 (dd, 1H), 7.86 (t, 1H), 6.93 (d, 2H), 6.88 (s, 2H), 6.81 (d, 2H), 3.82 (s, 3H), 2.43 (s, 3H), 2.29 (s, 3H), 2.22 (s, 3H), 2.00 (s, 6H).

9. Preparation of 2-[1-(2,4,6-trimethylphenylimino)ethyl]-6-[1-(4-methoxyphenylimino) ethyl] pyridine iron [II] chloride complex (7)

(7)

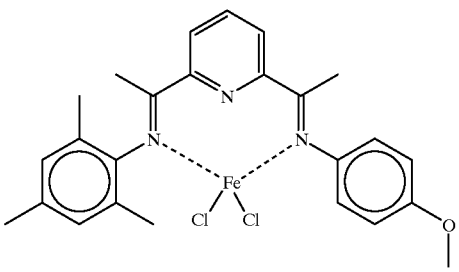

In an inert atmosphere a solution of 133 mg diimine (6, 0.34 mmol) in 15 ml dichloromethane was added to 40 mg FeCl$_2$ (0.31 mmol) in 5 ml dichloromethane. The mixture was stirred at ambient temperature for 72 hours. Addition of 10 ml hexane yielded a blue precipitate, which was isolated by centrifugation and dried in vacuo. Yield 120 mg (74%) of iron complex 7. $^1$H-NMR (CD$_2$Cl$_2$, broad signals) δ 82.2 (1H, Py-H$_m$), 81.5 (1H, Py-H$_m$), 23.2 (1H, Py-H$_p$) 20.1 (3H, Me), 16.0 (6H, Me), 15.6 (2H, ArH), 12.9 (2H, ArH), 4.9 (3H, MeO), −5.3 (3H, MeC=N), −19.6 (2H, ArH), −31.6 (3H, MeC=N).

10. Preparation of 4-trimethylsiloxy-aniline (8)

To a 100-ml three-necked flask equipped with a magnetic stirring bar, dropping funnel, reflux condenser, bubble counter and gas discharge tube containing 4-hydroxy-aniline (18.5 g, 0.17 mol) hexamethyldisilazane (14.6 g, 0.09 mol) was rapidly added drop-wise at room temperature. After the addition of three drops of trimethylchlorosilane as the catalyst, the heterogeneous mixture was slowly heated. Evolution of ammonia becomes noticeable at 50° C. and became very vigorous at 125° C. The temperature was raised to 150° C., where it was maintained until gas evolution ceased. The homogeneous liquid is then purified by distillation using a vigreux column. The fraction distilling at 85° C. and 2 mbar was compound 8 (yield: 85%). $^1$H NMR (CDCl$_3$) δ 6.65 (d-AB, 2H), 6.55 (d-AB, 2H), 3.38 (s, 2H), 0.21 (s, 9H).

11. Preparation of 2-[1-(2,4,6-trimethylphenylimino)ethyl]-6-[1-(4-trimethylsiloxyphenylimino)ethyl]pyridine (9)

(9)

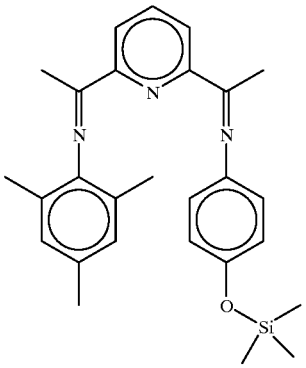

Monoimine (1, 1.4 g, 5 mmol) and 4-trimethylsiloxyaniline (8, 906 mg, 5 mmol) were dissolved in 50 ml of toluene. To this solution 4 Å molecular sieves were added. After standing at room temperature for 4 days with addition of more molecular sieves the reaction mixture was filtered and the solvent was removed in vacuo. The product was washed with a small amount of methanol. Yield 1.4 g (63%) of mixed diimine (9). $^1$H NMR (CDCl$_3$) δ 8.42 (dd, 1H), 8.33 (dd, 1H), 7.86 (t, 1H), 6.88 (s, 2H), 6.86 (d, 2H), 6.74 (d, 2H), 2.42 (s, 3H), 2.28 (s, 3H), 2.21 (s, 3H), 2.00 (s, 6H), 0.27 (s, 9H).

12. Preparation of 2-[1-(2,4,6-trimethylphenylimino)ethyl]-6-[1-(4-trimethylsiloxyphenylimino)ethyl]pyridine iron [II] chloride complex (10)

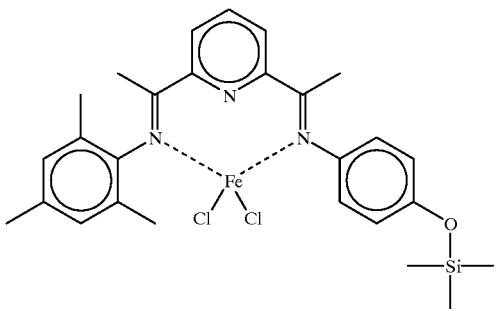

(10)

In an inert atmosphere a solution of 100 mg diimine (9, 0.22 mmol) in 4 ml dichloromethane was added to 26 mg FeCl$_2$ (0.20 mmol) in 3 ml dichloromethane. The mixture was stirred at ambient temperature for 20 hrs. Addition of 8 ml hexane yielded a blue precipitate, which was isolated by centrifugation and dried in vacuo. Yield 35 mg (30%) of iron complex 10. $^1$H-NMR showed besides compound 10, the presence of a second iron complex (ca. 20%): presumably the 4-trimethylsiloxy group is partially hydrolysed to the hydroxyl group. The iron complex 10 was used without further purification in ethylene oligomerisation reactions.

$^1$H-NMR (CD$_2$Cl$_2$, broad signals, selective data) δ 81.6 (2H, Py-H$_m$), 20.5 (3H, Me), 15.2 (2H, ArH), 15.1 (6H, Me), 12.5 (2H, ArH), -0.6 (9H, OSiMe$_3$), -5.5 (3H, MeC=N), -21.1 (2H, o-ArH), -30.5 (3H, MeC=N).

13. Methylaluminoxane (MAO)

The MAO-solution (10.1% wt in toluene, [Al] 4.97% wt) used was ex. Witco GmbH, Bergkamen, Germany.

14. Methylaluminoxane, modified, in heptane (MMAO-3A in heptane)

The MMAO-3A in heptane (MMAO; [Al] =6.42% wt) used in Example B (comparative), was purchased from Akzo-Nobel Chemicals B. V., Amersfoort, The Netherlands.

Catalyst System Preparation

Catalyst preparation was carried out under nitrogen in a Braun MB 200-G dry box.

The iron complex (typically about 10 mg) was placed in a reaction vessel; the MAO-solution (4.0 g), of the above mentioned grade, was added and stirred for 2 minutes. This yielded generally a red solution. Thereafter toluene (9.0 g) was added and the solution was stirred for another 15 min. Immediately hereafter, part of this solution was used in the oligomerisation reaction (see Table 1 for the amounts used). In comparative Example B the iron complex XI was added to the reactor without pre-activation with MAO or MMAO.

Oligomerisation Experiments

Oligomerisation experiments were carried out in a 1-liter steel autoclave equipped with jacket cooling with a heating/cooling bath (ex. Julabo, model no. ATS-2) and a turbine/gas stirrer and baffles, or in a similarly equipped 0.5-litre steel autoclave (as indicated in Table 1 and the description of the experiment). In order to remove traces of water from the reactor, it was evacuated overnight at <10 Pa, at 70° C. The reactor was scavenged by introducing 250 ml toluene (or isooctane) and MAO (0.3–1.2 g solution) and subsequent stirring at 50° C. under nitrogen pressure of 0.4–0.5 MPa for 30 min. The reactor contents were discharged via a tap in the base of the autoclave. The reactor was evacuated to 0.4 kPa and loaded with 250 ml toluene (or isooctane), in the case of a 1-litre reactor, and heated to 40° C. and pressurised with ethylene to the pressure indicated in Table 1 or in the description of the Experiment. The MAO-solution (typically 0.5 g for the 1-litre reactor) was then added to the reactor and the stirring was continued for 30 minutes (for the 0.5-litre reactor the amounts of solvent and MAO were halved). The catalyst system prepared as described above and in an amount as described in Table 1, was introduced into the stirred reactor using an injection system, which was rinsed twice with 10 ml toluene (or isooctane). Addition of the catalyst solution resulted in an exotherm (generally 5–20° C.), which reached a maximum within 1 minute and was followed by rapid establishment of the temperature indicated in Table 1. Temperature and pressure were monitored throughout the reaction, as well as ethylene consumption, whilst maintaining a constant ethylene pressure. After consuming a certain volume ethylene, the oligomerisation was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5–3.5 g) (ex. Aldrich) as internal standard to the crude product the amount of C$_4$–C$_{30}$ olefins was determined by gas chromatography, from which the K-factor was determined by regression analysis, using the C$_6$–C$_{28}$ data. From this regression analysis, the theoretical contents of C$_{30}$–C$_{100}$ components, i.e. waxy solids, was calculated. These data are reported in Table 1.

The amount of solids in the product was determined as follows. The crude reaction product was centrifuged at 4000 rpm for 30 min after which the clear upper layer was decanted. The lower layer consisting of solid olefins, toluene and a minor amount of liquid olefins was mixed with 500 ml acetone and filtered off over a glass filter (porosity P3). The solid product was dried for 24 hours at 70° C. at <1 kpa, weighed and its <C$_{30}$ contents determined by gas chromatography of a 1,2-dichlorobenzene or a 1,2,4-trichlorobenzene solution of the solids. The amounts of solids reported in Table 1 are the isolated solids having a carbon number>C$_{28}$.

The relative amounts of the linear 1-hexene amongst all hexene isomers and the relative amount of 1-dodecene amongst all dodecene isomers were evaluated by GC analysis and are reported in Table 1.

EXAMPLE A

Comparative

Iron complex XI (prepared according to WO-A-99/02472) was employed in toluene in an experiment similar to Experiment Number 16 of WO-A-99/02472. The catalyst gave an oligomerisation mixture having a K-factor of 0.774, as derived from regression analysis using the C$_6$–C$_{28}$ contents, determined by GC. C$_4$ is left out of the regression analysis, since its volatility hinders reliable GC-measurements. The details of Example A are given in Table 1. From this K-factor a C$_{20}$–C$_{28}$ fraction of 19.7% wt and a C$_{30}$–C$_{100}$ fraction of 12.2% wt on total product can be calculated. The amount of solids>$C_{28}$ on total ethylene intake was 53.8% wt (the ethylene intake is assumed to be equal to the total oligomerisation product, i.e. $C_4$–$C_{100}$ olefins) This corroborates that the distribution deviates greatly from Schulz-Flory, giving rise to larger than expected amounts of higher molecular weight compounds, i.e. solid waxes. This deviation is also clear from FIG. 1 in which the regression analysis is represented graphically (for 12 observations $R^2$=0.97 and standard error=0.07).

EXAMPLE B

Comparative

An experiment with iron complex XI (prepared according to WO-A-99/02472) was carried out in isooctane with modified methylaluminoxane in heptane (MMAO) as scavenger/co-catalyst and using a mode of iron complex XI addition similar to that described in Experiment number 20 of WO-A-99/02472. To that end 101 mg of a dichloromethane solution of complex XI (9 mg) in dry dichloromethane (20.5 g) was added to the 1-litre autoclave, loaded with 250 ml of isooctane and 430 mg of MMAO (see Table 1 for experimental details). This method of catalyst addition gave rise to an oligomerisation mixture having a K-factor of 0.834 (regression statistics being: $R^{12}$=0.98; standard error=0.05 for 12 observations). From this K-factor a $C_{20}$–$C_{28}$ fraction of 23.2% wt and a $C_{30}$–$C_{100}$ fraction of 26.8% wt on total product can be calculated. The amount of solids>$C_{28}$ isolated on total product was, however, 68.2% wt. This confirms again that the distribution deviates greatly from Schulz-Flory, giving rise to larger than expected high molecular weight compounds.

EXAMPLE C

Comparative

Using the iron complex X in an experiment similar to Experiment number 13 of Table 1 of WO-A-99/02472, similar phenomena were observed (see comparative Example C in Table 1 for details). The amount of solids (having a carbon number>$C_{28}$) isolated was 11.1% wt on total product, whilst on the basis of the K-factor of 0.737 (as derived from the $C_8$–$C_{28}$ contents by regression analysis) a $C_{30}$–$C_{100}$ fraction of 7.0% wt on total product has to be expected. Hence, a clear deviation from Schulz-Flory distribution, giving rise to a larger amount of high molecular weight compounds than calculated. The regression analysis using the $C_6$–$C_{28}$ contents, as given in FIG. 2 also shows a clear deviation from Schulz-Flory distribution at higher carbon numbers (for 12 observations $R^2$=0.98 and standard error 0.06).

Experiments 1 and 2

Experiments 1 and 2 were carried out at an ethylene pressure of 1.6 MPa, i.e. 1.5 MPa (gauge), using the non-symmetrical iron complex (3) which is in accordance with the present invention, under conditions similar to the above-mentioned Comparative Experiment C. Experimental details are given in Table 1. The regression analysis for Experiments 1 and 2, using the $C_6$–$C_{28}$ contents, as shown for Experiment 1 in FIG. 3, gives a nearly perfect Schulz-Flory distribution over the whole range of oligomers. The K-factors are 0.747 and 0.749 for Experiments 1 and 2, respectively (for 12 observations $R^2$=1.00 and standard error=0.02 in both experiments). This is confirmed by the amounts of waxy solids>$C_{28}$ isolated on total product of 6.6 and 7.5% wt for Experiment 1 and 2, respectively, whereas the respective K-factors give rise to $C_{30}$–$C_{100}$ fractions on total oligomerisation product of 8.2 and 8.5% wt for Experiments 1 and 2 (the fact that less solids>$C_{28}$ are isolated than theoretically expected, is due to their solubility in the toluene-solution of the <$C_{28}$ oligomers). The hexenes of both Experiments 1 and 2 have the following composition 1-hexene=99.7% wt, cis-2-hexene=0.0% wt, trans-2-hexene=0.0% wt, 3-hexenes=0.0% wt, branched hexenes=0.2% wt.

In conclusion it may be stated that no deviation from Schulz-Flory distribution is observed, which translates to the formation of less high molecular weight products in comparison with (comparative) Examples A-C. This has the advantage of more straightforward processing (less clogging by solids in the plants and its work-up train) and of less need for reprocessing of high molecular weight olefins (to render the technology economically feasible). Moreover, besides these advantages, the non-symmetrical iron catalyst has the following advantages over the catalyst according to WO-A-99/02472 (see Comparative Example C in Table 1):

1. the catalyst activity (T.O.F) is at least on a par or even higher.
2. the purity of the alpha olefins, particularly that of 1-dodecene, is significantly higher.

Experiment 3

Experiment 3 is a repeat of Experiments 1 and 2 at a lower ethylene intake and using a 0.5-litre steel autoclave at ethylene pressures of 1.6 MPa. Experimental details are mentioned in Table 1. Once again, regression analysis using the $C_6$–$C_{28}$ contents gives a nearly perfect Schulz-Flory distribution, having K-factor of 0.727 and the following regression statistics for 12 observations: $R^2$=1.00 and standard error=0.02. The Schulz-Flory distribution is yet again confirmed by the isolated amount of waxy solids>$C_{28}$, which is lower than the amounts calculated from the K-factor. A result of the lower final alpha olefin concentration, this Experiment has an even higher 1-dodecene purity of 98.6% wt in comparison with 98.1 and 98.0% wt for Experiments 1 and 2, respectively.

Experiment 4

In this Experiment, the ethylene pressure was raised to 2.3 MPa, again using a 0.5-litre steel autoclave. The regression analysis as shown in FIG. 4 again gives nearly perfect Schulz-Flory distributions, having a K-factor of 0.708 showing the following statistics for 12 observations: $R^2$=1.00 and standard error=0.02. This is confirmed by the amount of solids>$C_{28}$ isolated, which are lower than the amounts calculated from the K-factor. Hence, Experiment 4 shows a lower K-factor than Experiment 3, whereas its 1-dodecene purity is the same or even better (see Table 1). In conclusion: by tuning the pressure, the K-factor, i.e. the oligomer distribution, and the product purity may be altered to what is required for economical operation.

Experiment 5

Experiment 5 is a repeat of Experiments 1 and 2 at a lower ethylene intake and using a 1-litre steel autoclave at ethylene pressures of 1.6 MPa, but now at a temperature of 70° C. Experimental details are mentioned in Table 1. Once again, regression analysis (see FIG. 5) using the $C_6$–$C_{28}$ contents gives a nearly perfect Schulz-Flory distribution, having K-factor of 0.732 and the following regression statistics for 12 observations: $R^2$=1.00 and standard error=0.02. The Schulz-Flory distribution is yet again confirmed by the isolated amount of waxy solids>$C_{28}$, which is lower than the amounts calculated from the K-factor. At this reaction temperature the 1-hexene and the 1-dodecene purity were 99.5 and 97.7% wt, respectively.

Experiment 6

This experiment was carried out similarly to Experiment 5 in toluene at 70° C. and an ethylene pressure of 1.6 MPa in a 1-litre steel autoclave and using iron complex (5), which is in accordance with the present invention. Experimental details are given in Table 1. The regression analysis (see FIG. 6) using the $C_6$–$C_{28}$ contents gives a nearly perfect Schulz-Flory distribution over the whole range of oligomers, giving rise to a K-factor of 0.785 (for 12 observations, $R^2$=1.00 and standard error=0.02). By comparison of the regression statistics with those of Comparative Example C, it is clear that Experiment 6 gives a nearly perfect Schulz-Flory distribution. This is confirmed by the isolated amount of solids>$C_{28}$ relative to the amount calculated from the K-factor. The product shows a 1-hexene and 1-dodecene purity of 99.6 and 98.6% wt, respectively. The hexenes have the following composition: 1-hexene=99.6, cis-2-hexene=0.0, trans-2-hexene=0.0, 3-hexenes=0.0, branched hexenes=0.4% wt.

Experiment 7

This experiment was carried out similarly to Experiment 3 in toluene at 50° C. and at an ethylene pressure of 1.6 MPa, but using iron complex (7) and a 1-liter steel autoclave, which is in accordance with the present invention. Experimental details are given in Table 1. The regression analysis using the $C_6$–$C_{28}$ contents gives a nearly perfect Schulz-Flory distribution over the whole range of oligomers, giving rise to a K-factor of 0.699 (for 12 observations, $R^2$=1.00 and standard error=0.01). By comparison of the regression statistics with those of Comparative Example C, it is clear that Experiment 7 gives a nearly perfect Schulz-Flory distribution. This is confirmed by the isolated amount of solids>$C_{28}$ relative to the amount calculated from the K-factor. The product shows a 1-hexene and 1-dodecene purity of 99.8 and 99.0% wt, respectively. The hexenes have the following composition: 1-hexene=99.8, internal hexenes=0.1, branched hexenes=0.1% wt.

Experiment 8

This experiment was carried out similarly to Experiment 7 in toluene at 50° C. in a 1-litre steel autoclave, but using iron complex (10) and an ethylene pressure of 1.7 MPa, which is in accordance with the present invention. Experimental details are given in Table 1. The regression analysis using the $C_6$–$C_{28}$ contents gives a nearly perfect Schulz-Flory distribution over the whole range of oligomers, giving rise to a K-factor of 0.726 (for 12 observations, $R^2$=1.00 and standard error=0.01). By comparison of the regression statistics with those of Comparative Example C, it is clear that Experiment 8 gives a nearly perfect Schulz-Flory distribution. This is confirmed by the isolated amount of solids>$C_{28}$ relative to the amount calculated from the K-factor. The product shows a 1-hexene and 1-dodecene purity of 99.8 and 98.8% wt, respectively. The hexenes have the following composition: 1-hexene=99.8, internal hexenes=0.1, branched hexenes=0.2% wt.

In conclusion, it may be stated that in the case of using a non-symmetrical iron complex no deviation from Schulz-Flory distribution occurs, which is beneficial to the economics of the overall process, since in this case no additional amounts of solids, i.e. heavy wax, are being formed which need to be processed (which may in itself be cumbersome due to clogging, etc. of the plant and/or its work-up train) by isomerisation and disproportionation with e.g. 2-butene to arrive at internal olefins in the economically attractive range ($C_8$–$C_{28}$). Moreover, the catalyst activity of these new catalysts is at least on a par with the state-of-the-art catalysts and the purity of the 1-alkenes is even higher.

These experiments prove the beneficial effects which can be achieved with the catalyst systems of the present invention. As explained above, these improvements are of major importance for the economic attractiveness of the process.

TABLE 1

| | Example No. | | |
|---|---|---|---|
| | Ex. A (comp)[1,2] | Ex. B (comp)[2,3] | Ex. C (comp)[2] |
| Iron Complex in Reactor (nmol) | 113 | 89 | 397 |
| Reaction Time (min) | 112 | 60 | 118 |
| Ethene Pressure MPa (bar(a)) | 1.6 (16) | 1.5 (15) | 1.6 (16) |
| Ethene consumed (Total Product) (g) | 47.2 | 37.3 | 352.2 |
| Isolated Product <$C_{30}$ (g) | 14.1 | 11.3 | 288.2 |
| Isolated Solids >$C_{28}$ (g) | 25.4 | 25.4 | 39.0 |
| Solids >$C_{28}$ on Ethene (% wt) | 53.8 | 68.2 | 11.1 |
| $C_{30-100}$ on Total Product (calc'd) (% wt) | 12.2 | 26.8 | 7.0 |
| T.O.F (mol $C_2$ = /mol Fe*h) | 7.98E + 06 | 1.49E + 07 | 1.62E + 07 |
| K-factor | 0.774 | 0.834 | 0.737 |
| 1-$C_6$ = purity (% wt) | 99.5 | 98.2 | 99.1 |
| 1-$C_{12}$ = purity (% wt) | 98.4 | 97.7 | 96.5 |

| | Example No. | | | |
|---|---|---|---|---|
| | Ex. 1 | Ex. 2 | Ex. 3[1] | Ex. 4[1] |
| Iron Complex in Reactor (nmol) | 204 | 209 | 108 | 85 |
| Reaction Time (min) | 176 | 95 | 13 | 16 |
| Ethene Pressure MPa (bar(a)) | 1.6 (16) | 1.6 (16) | 1.6 (16) | 2.3 (23) |
| Ethene consumed (Total Product) (g) | 352.2 | 352.2 | 48.2 | 47.8 |
| Isolated Product <$C_{30}$ (g) | 322.8 | 310.7 | 45.0 | 41.3 |
| Isolated Solids >$C_{28}$ (g) | 23.4 | 26.5 | 1.0 | 0.9 |
| Solids >$C_{28}$ on Ethene (% wt) | 6.6 | 7.5 | 2.1 | 1.9 |
| $C_{30-100}$ on Total Product (calc'd) (% wt) | 8.2 | 8.5 | 6.0 | 4.4 |
| T.O.F (mol $C_2$ = /mol Fe*h) | 2.10E + 07 | 3.82E + 07 | 7.34E + 07 | 7.50E + 07 |
| K-factor | 0.747 | 0.749 | 0.727 | 0.708 |
| 1-$C_6$ = purity (% wt) | 99.7 | 99.7 | 99.7 | 99.8 |
| 1-$C_{12}$ = purity (% wt) | 98.1 | 98.0 | 98.6 | 98.9 |

| | Example No. | | | |
|---|---|---|---|---|
| | Ex. 5[4] | Ex. 6[4] | Ex. 7 | Ex. 8 |
| Iron Complex in Reactor (nmol) | 169 | 274 | 245 | 281 |
| Reaction Time (min) | 26 | 56 | 71 | 90 |
| Ethene Pressure MPa (bar(a)) | 1.6 (16) | 1.6 (16) | 1.6 (16) | 1.7 (17) |
| Ethene consumed (Total Product) (g) | 136.3 | 135.7 | 70.4 | 117.4 |
| Isolated Product <$C_{30}$ (g) | 119.7 | 112.5 | 66.8 | 103.1 |
| Isolated Solids >$C_{28}$ (g) | 5.6 | 15.7 | 0.8 | 3.6 |
| Solids >$C_{28}$ on Ethene (% wt) | 4.1 | 11.6 | 1.2 | 3.1 |
| $C_{30-100}$ on Total Product (calc'd) (% wt) | 6.5 | 14.1 | 3.8 | 5.9 |
| T.O.F (mol $C_2$ = /mol Fe*h) | 6.74E + 07 | 1.90E + 07 | 8.67E + 06 | 1.00E + 07 |
| K-factor | 0.732 | 0.785 | 0.699 | 0.726 |

TABLE 1-continued

| | | | | |
|---|---|---|---|---|
| 1-$C_6$ = purity (% wt) | 99.5 | 99.6 | 99.8 | 99.8 |
| 1-$C_{12}$ = purity (% wt) | 97.7 | 98.6 | 99.0 | 98.0 |

Experiments carried out at 50° C., at [Al]/[Fe] ratio of 2500–6000 in toluene, using 1-liter steel autoclave, unless indicated otherwise.
[1]Carried out in 0.5-liter steel autoclave.
[2]Catalyst prepared according to WO-A-99/02472.
[3]Complex XI in dichloromethane (without pre-activation) added to MMAO/isooctane mixture at [Al]/[Fe] ratio of 11500.
[4]Carried out at 70° C.; ethene consumption derived from total product ($C_4$–$C_{100}$ olefins from regression analysis).

We claim:

1. A non-symmetrical bis-aryliminepyridine ligand of formula (I),

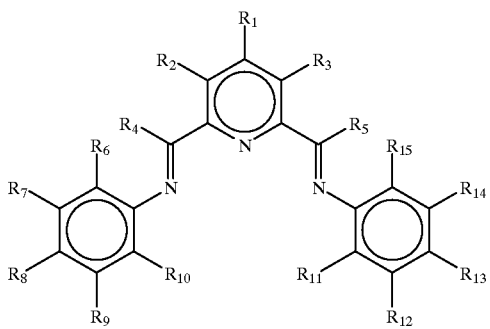

(I)

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ and $R_{10}$ are each, independently, inert functional group or primary or secondary carbon atom group provided that $R_6$ and $R_{10}$ are not both a secondary carbon atom group, and $R_{11}$ and $R_{15}$ are, independently, hydrogen or halide.

2. The non-symmetrical bis-aryliminepyridine ligand of claim 1 wherein $R_6$ and $R_{10}$ are each, independently, primary or secondary carbon atom group provided that $R_6$ and $R_{10}$ are not both a secondary carbon atom.

3. A non-symmetrical bis-aryliminepyridine ligand of formula (I),

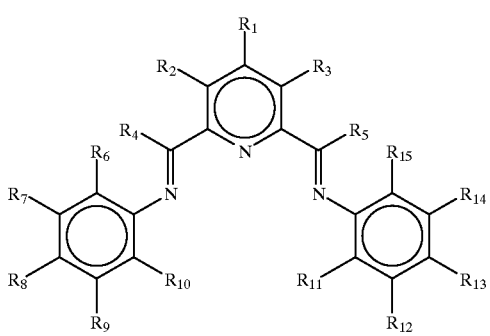

(I)

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ and $R_{10}$ are each, independently, inert functional group or primary or secondary carbon atom group provided that $R_6$ and $R_{10}$ are not both a secondary carbon atom group, and $R_{11}$ and $R_{15}$ are hydrogen.

4. The non-symmetrical bis-aryliminepyridine ligand of claim 3 wherein $R_6$ and $R_{10}$ are each, independently, primary or secondary carbon atom group provided that $R_6$ and $R_{10}$ are not both a secondary carbon atom.

5. The non-symmetrical bis-aryliminepyridine ligand of claim 1 wherein $R_6$ and $R_{10}$ are each, independently, primary carbon atom group.

6. The bis-aryliminepyridine $MX_n$ complex comprising a non-symmetrical ligand of claim 1, and wherein M is a metal atom selected from Fe or Co, n is 2 or 3, and X is halide, optionally substituted hydrocarbyl, alkoxide, amide, or hydride.

7. The bis-aryliminepyridine $MX_n$ complex of claim 6 wherein $R_6$ and $R_{10}$ of the non-symmetrical ligand are each, independently, primary or secondary carbon atom group provided that $R_6$ and $R_{10}$ are not both a secondary carbon atom.

8. The bis-aryliminepyridine $MX_n$ complex of claim 6 wherein $R_{11}$ and $R_{15}$ of the bis-aryliminepyridine ligand are hydrogen.

9. The bis-aryliminepyridine $MX_n$ complex of claim 7 wherein $R_{11}$ and $R_{15}$ are hydrogen.

10. The bis-aryliminepyridine $MX_n$ complex of claim 6 wherein $R_6$ and $R_{10}$ of the non-symmetrical bis-aryliminepyridine ligand are each, independently, primary carbon atom group.

11. A [bis-aryliminepyridine $MY_p.L_n^+$][$NC^-$]$_q$ complex comprising a non-symmetrical ligand of claim 1, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

12. The [bis-aryliminepyridine $MY_p.L_n^+$][$NC^-$]$_q$ complex of claim 11 wherein $R_6$ and $R_{10}$ of the non-symmetrical ligand are each, independently, primary or secondary carbon atom group provided that $R_6$ and $R_{10}$ are not both a secondary carbon atom.

13. The [bis-aryliminepyridine $MY_p.L_n^+$][$NC^-$]$_q$ complex of claim 11 wherein $R_{11}$ and $R_{15}$ of the bis-aryliminepyridine ligand are hydrogen.

14. The [bis-aryliminepyridine $MY_p.L_n^+$][$NC^-$]$_q$ complex of claim 12 wherein $R_{11}$ and $R_{15}$ are hydrogen.

15. The [bis-aryliminepyridine $MY_p.L_n^+$][$NC^-$]$_q$ complex of claim 11 wherein wherein $R_6$ and $R_{10}$ of the non-symmetrical bis-aryliminepyridine ligand are each, independently, primary carbon atom group.

16. A non-symmetrical bis-aryliminepyridine ligand of formula (I),

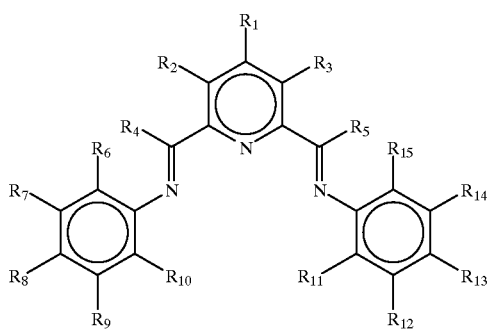

(I)

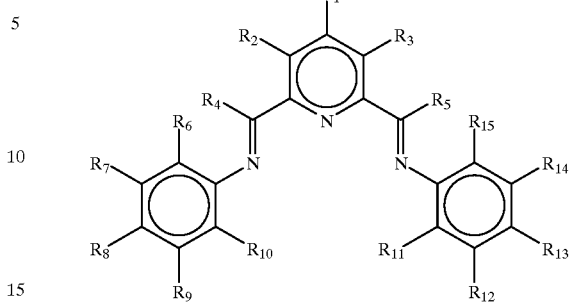

(I)

wherein wherein $R_1$–$R_3$ are hydrogen, $R_4$, $R_5$, $R_6$, $R_8$ and $R_{10}$ are methyl, $R_7$, $R_9$, $R_{11}$, $R_{12}$, $R_{14}$ and $R_{15}$ are hydrogen; and $R_{13}$ is tertiary-butyl.

17. The bis-aryliminepyridine $MX_n$ complex comprising a non-symmetrical ligand of claim 16, and wherein M is a metal atom selected from Fe or Co, n is 2 or 3, and X is halide, optionally substituted hydrocarbyl, alkoxide, amide, or hydride.

18. A [bis-aryliminepyridine $MY_p.L_n^+$][$NC^-$]$_q$ complex comprising a non-symmetrical ligand of claim 16, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1 or 2.

19. A non-symmetrical bis-aryliminepyridine ligand of formula (I), wherein $R_{1-3}$ are hydrogen, $R_4$, $R_5$, $R_6$, $R_8$ and $R_{10}$ are methyl, $R_7$, $R_9$, $R_{11}$, $R_{12}$, $R_{14}$ and $R_{15}$ are hydrogen, and $R_{13}$ is trimethylsiloxy.

23. The bis-aryliminepyridine $MX_n$ complex comprising a non-symmetrical ligand of claim 22, and wherein M is a metal atom selected from Fe or Co, n is 2 or 3, and X is halide, optionally substituted hydrocarbyl, alkoxide, amide, or hydride.

24. A [bis-aryliminepyridine $MY_p.L_n^+$][$NC^-$]$_q$ complex comprisng a non-symmetrical ligand of claim 22, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1 or 2.

25. A non-symmetrical bis-aryliminepyridine ligand of formula (I),

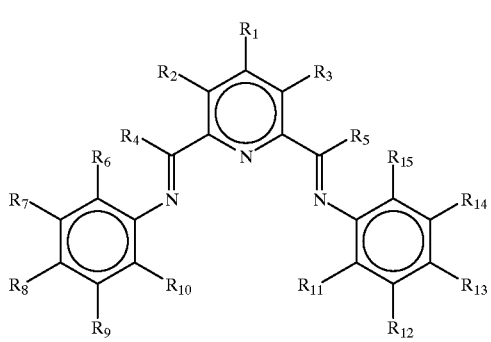

(I)

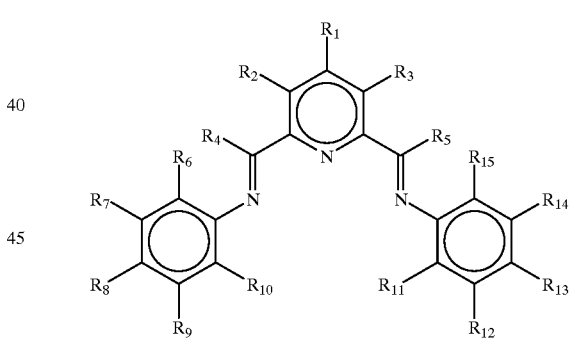

(I)

wherein $R_{1-3}$ are hydrogen, $R_4$, $R_5$, $R_6$, $R_8$ and $R_{10}$ are methyl, $R_7$, $R_9$, $R_{11}$, $R_{12}$, $R_{14}$ and $R_{15}$ are hydrogen, and $R_{13}$ is methoxy.

20. The bis-aryliminepyridine $MX_n$ complex comprising a non-symmetrical ligand of claim 19, and wherein M is a metal atom selected from Fe or Co, n is 2 or 3, and X is halide, optionally substituted hydrocarbyl, alkoxide, amide, or hydride.

21. A [bis-aryliminepyridine $MY_p.L_n^+$][$NC^-$]$_q$ complex comprising a non-symmetrical ligand of claim 19, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1 or 2.

22. A non-symmetrical bis-aryliminepyridine ligand of formula (I), wherein $R_1$–$R_3$ are hydrogen, $R_4$, $R_5$, $R_6$, $R_8$ and $R_{10}$ are methyl, $R_7$, $R_9$, $R_{12}$, $R_{13}$, $R_{14}$ and $R_{15}$ are hydrogen, and $R_{11}$ is fluoride.

26. The bis-aryliminepyridine $MX_n$ complex comprising a non-symmetrical ligand of claim 25, and wherein M is a metal atom selected from Fe or Co, n is 2 or 3, and X is halide, optionally substituted hydrocarbyl, alkoxide, amide, or hydride.

27. A [bis-aryliminepyridine $MY_p.L_n^+$][$NC^-$]$_q$ complex comprising a non-symmetrical ligand of claim 25, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

28. The non-symmetrical bis-aryliminepyridine ligand of claim 1 wherein $R_4$ and $R_5$ are methyl, hydrogen or phenyl.

29. The non-symmetrical bis-arylimineypyridine ligand of claim 1 wherein $R_1$ to $R_3$ are hydrogen.

30. The bis-arylimineypyridine $MX_n$ complex of claim 6 wherein $R_4$ and $R_5$ of the bis-arylimineypyridine ligand are methyl, hydrogen or phenyl.

31. The bis-arylimineypyridine $MX_n$ complex of claim 30 wherein $R_1$ to $R_3$ of the bis-arylimineypyridine ligand are hydrogen.

32. The bis-arylimineypyridine $MX_n$ complex of claim 6 wherein M is Fe.

33. The bis-arylimineypyridine $MX_n$ complex of claim 6 wherein X is halide.

34. The [bis-arylimineypyridine $MY_p.L_n^+][NC^-]_q$ complex of claim 11 wherein $R_4$ and $R_5$ of the non-symmetrical ligand are methyl, hydrogen or phenyl.

35. The [bis-arylimineypyridine $MY_p.L_n^+][NC^-]_q$ complex of claim 34 wherein $R_1$ to $R_3$ of the non-symmetrical ligand are hydrogen.

36. The [bis-arylimineypyridine $MY_p.L_n^+][NC^-]_q$ complex of claim 11 wherein M is Fe.

37. A non-symmetrical bis-arylimineypyridine ligand of formula (I),

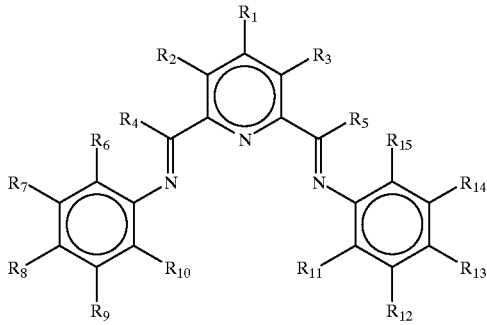

(I)

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ is taken together with $R_7$ to form a ring, $R_{10}$ is a primary carbon atom group, an inert functional group, hydrogen, and $R_{11}$ and $R_{15}$ are, independently, hydrogen or halide.

38. The non-symmetrical bis-arylimineypyridine ligand of claim 37 wherein $R_4$ and $R_5$ are methyl, hydrogen or phenyl.

39. The non-symmetrical bis-arylimineypyridine ligand of claim 37 wherein $R_1$ to $R_3$ are hydrogen.

40. The bis-arylimineypyridine $MX_n$ complex comprising a non-symmetrical ligand of claim 37, and wherein M is a metal atom selected from Fe or Co, n is 2 or 3, and X is halide, optionally substituted hydrocarbyl, alkoxide, amide, or hydride.

41. The bis-arylimineypyridine $MX_n$ complex of claim 40, wherein M is Fe.

42. The bis-arylimineypyridine $MX_n$ complex of claim 40 wherein X is halide.

43. The bis-arylimineypyridine $MX_n$ complex of claim 40 wherein $R_4$ and $R_5$ of the bis-arylimineypyridine ligand are methyl, hydrogen or phenyl.

44. The bis-arylimineypyridine $MX_n$ complex of claim 40 wherein $R_1$ to $R_3$ of the bis-arylimineypyridine ligand are hydrogen.

45. A [bis-arylimineypyridine $MY_p.L_n^+][NC^-]_q$ complex comprising a non-symmetrical ligand of claim 37, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

46. The [bis-arylimineypyridine $MY_p.L_n^+][NC^-]_q$ complex of claim 45 wherein M is Fe.

47. The [bis-arylimineypyridine $MY_p.L_n^+][NC^-]_q$ complex of claim 45 wherein $R_4$ and $R_5$ of the non-symmetrical ligands are methyl, hydrogen or phenyl.

48. A non-symmetrical bis-arylimineypyridine ligand of formula (I),

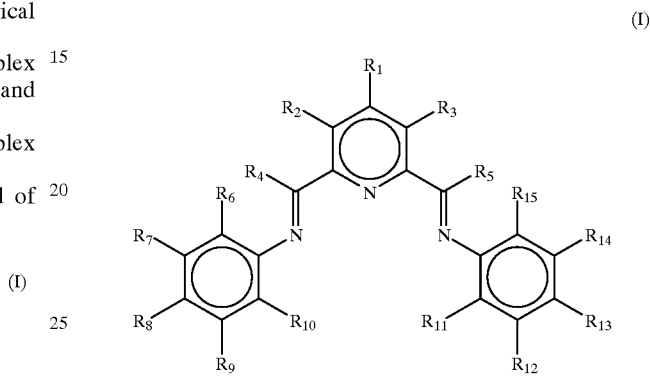

(I)

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ and $R_{10}$ are taken together with $R_7$ and $R_9$ respectively to form a rings, and $R_{11}$ and $R_{15}$ are, independently, hydrogen or halide.

49. The non-symmetrical bis-arylimineypyridine ligand of claim 48 wherein $R_4$ and $R_5$ are methyl, hydrogen or phenyl.

50. The non-symmetrical bis-arylimineypyridine ligand of claim 48 wherein $R_1$ to $R_3$ are hydrogen.

51. The bis-arylimineypyridine $MX_n$ complex comprising a non-symmetrical ligand of claim 48, and wherein M is a metal atom selected from Fe or Co, n is 2 or 3, and X is halide, optionally substituted hydrocarbyl, alkoxide, amide, or hydride.

52. The bis-arylimineypyridine $MX_n$ complex of claim 51 wherein M is Fe.

53. The bis-arylimineypyridine $MX_n$ complex of claim 51 wherein X is halide.

54. The bis-arylimineypyridine $MX_n$ complex of claim 51 wherein $R_4$ and $R_5$ of the bis-arylimineypyridine ligand are methyl, hydrogen or phenyl.

55. The bis-arylimineypyridine $MX_n$ complex of claim 51 wherein $R_1$ to $R_3$ of the bis-arylimineypyridine ligand are hydrogen.

56. A [bis-arylimineypyridine $MY_p.L_n^+][NC^-]_q$ complex comprising a non-symmetrical ligand of claim 48, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

57. The [bis-arylimineypyridine $MY_p.L_n^+][NC^-]_q$ complex of claim 56 wherein M is Fe.

58. The [bis-arylimineypyridine $MY_p.L_n^+][NC^-]$ complex of claim 56 wherein $R_4$ and $R_5$ of the non-symmetrical ligand are methyl, hydrogen or phenyl.

59. A non-symmetrical bis-arylimineypyridine ligand of formula (I),

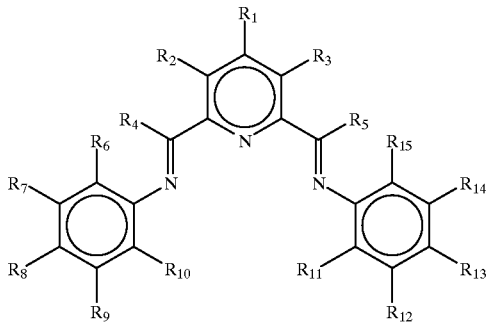

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$ and $R_{10}$ are, independently, methyl, ethyl, or linked to $R_7$ and $R_9$ respectively to form an anthracene skeleton, and $R_{11}$ and $R_{15}$ are, independently, hydrogen, fluoride or chloride.

60. The non-symmetrical bis-aryliminepyridine ligand of claim 59 wherein $R_4$ and $R_5$ are methyl, hydrogen or phenyl.

61. The non-symmetrical bis-aryliminepyridine ligand of claim 59 wherein $R_1$ to $R_3$ are hydrogen.

62. The bis-aryliminepyridine $MX_n$ complex comprising a non-symmetrical ligand of claim 59, and wherein M is a metal atom selected from Fe or Co, n is 2 or 3, and X is halide, optionally substituted hydrocarbyl, alkoxide, amide, or hydride.

63. The bis-aryliminepyridine $MX_n$ complex of claim 62 wherein M is Fe.

64. The bis-aryliminepyridine $MX_n$ complex of claim 62 wherein X is halide.

65. The bis-aryliminepyridine $MX_n$ complex of claim 62 wherein $R_4$ and $R_5$ of the bis-aryliminepyridine ligand are methyl, hydrogen or phenyl.

66. The bis-aryliminepyridine $MX_n$ complex of claim 62 wherein $R_1$ to $R_3$ of the bis-aryliminepyridine ligand are hydrogen.

67. A [bis-aryliminepyridine $MY_p.L_n^+$][$NC^-$]$_q$ complex comprising a non-symmetrical ligand of claim 59, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

68. The [bis-aryliminepyridine $MY_p.L_n^+$][$NC^-$]$_q$ complex of claim 67 wherein M is Fe.

69. The [bis-aryliminepyridine $MY_p.L_n^+$][$NC^-$] complex of claim 67 wherein $R_4$ and $R_5$ of the non-symmetrical ligand are methyl, hydrogen or phenyl.

70. The non-symmetrical bis-aryliminepyridine ligand of claim 3 wherein $R_6$ and $R_{10}$ are each, independently, primary carbon atom group.

71. The bis-aryliminepyridine $MX_n$ complex comprising a non-symmetrical ligand of claim 3, and wherein M is a metal atom selected from Fe or Co, n is 2 or 3, and X is halide, optionally substituted hydrocarbyl, alkoxide, amide, or hydride.

72. The bis-aryliminepyridine $MX_n$ complex of claim 71 wherein $R_6$ and $R_{10}$ of the non-symmetrical ligand are each, independently, primary or secondary carbon atom group provided that $R_6$ and $R_{10}$ are not both a secondary carbon atom.

73. The bis-aryliminepyridine $MX_n$ complex of claim 71 wherein $R_6$ and $R_{10}$ of the non-symmetrical bis-aryliminepyridine ligand are each, independently, primary carbon atom group.

74. A [bis-aryliminepyridine $MY_p.L_n^+$][$NC^-$]$_q$ complex comprising a non-symmetrical ligand of claim 3, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

75. The [bis-aryliminepyridine $MY_p.L_n^+$][$NC^-$]$_q$ complex of claim 74 wherein $R_6$ and $R_{10}$ of the non-symmetrical ligand are each, independently, primary or secondary carbon atom group provided that $R_6$ and $R_{10}$ are not both a secondary carbon atom.

76. The [bis-aryliminepyridine $MY_p.L_n^+$][$NC^-$]$_q$ complex of claim 74 wherein $R_6$ and $R_{10}$ of the non-symmetrical bis-aryliminepyridine ligand are each, independently, primary carbon atom group.

77. A non-symmetrical bis-aryliminepyridine ligand of formula (I),

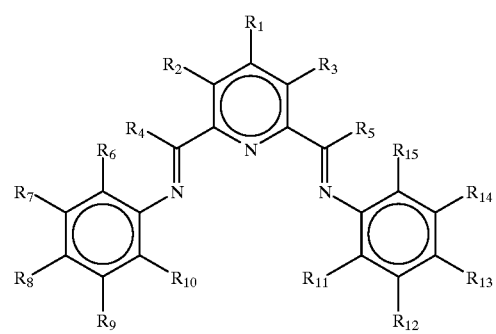

wherein $R_1$–$R_5$ and $R_7$–$R_9$ and $R_{12}$ and $R_{14}$ are each, independently, hydrogen, optionally substituted hydrocarbyl, an inert functional group, or any two of $R_1$–$R_3$ and $R_7$–$R_9$ vicinal to one another taken together may form a ring, and $R_6$ and $R_{10}$ are each, independently, inert functional group or primary or secondary carbon atom group provided that $R_6$ and $R_{10}$ are not both a secondary carbon atom group, and $R_{11}$ and $R_{15}$ are, independently, hydrogen or halide; and $R_{13}$ is tertiary-butyl.

78. The non-symmetrical bis-aryliminepyridine ligand of claim 77 wherein $R_6$ and $R_{10}$ are each, independently, primary or secondary carbon atom group provided that $R_6$ and $R_{10}$ are not both a secondary carbon atom.

79. The non-symmetrical bis-aryliminepyridine ligand of claim 77 wherein $R_{11}$ and $R_{15}$ are hydrogen.

80. The non-symmetrical bis-aryliminepyridine ligand of claim 78 wherein $R_{11}$ and $R_{15}$ are hydrogen.

81. The non-symmetrical bis-aryliminepyridine ligand of claim 77 wherein $R_6$ and $R_{10}$ are each, independently, primary carbon atom group.

82. The bis-aryliminepyridine $MX_n$ complex comprising a non-symmetrical ligand of claim 77, and wherein M is a metal atom selected from Fe or Co, n is 2 or 3, and X is halide, optionally substituted hydrocarbyl, alkoxide, amide, or hydride.

83. The bis-aryliminepyridine $MX_n$ complex of claim 82 wherein $R_6$ and $R_{10}$ of the non-symmetrical ligand are each, independently, primary or secondary carbon atom group provided that $R_6$ and $R_{10}$ are not both a secondary carbon atom.

84. The bis-aryliminepyridine $MX_n$ complex of claim 82 wherein $R_{11}$ and $R_{15}$ of the bis-aryliminepyridine ligand are hydrogen.

85. The bis-aryliminepyridine $MX_n$ complex of claim 83 wherein $R_{11}$ and $R_{15}$ are hydrogen.

86. The bis-aryliminepyridine $MX_n$ complex of claim 82 wherein $R_6$ and $R_{10}$ of the non-symmetrical bis-aryliminepyridine ligand are each, independently, primary carbon atom group.

87. A [bis-aryliminepyridine $MY_p \cdot L_n^+$][$NC^-$]$_q$ complex comprising a non-symmetrical ligand of claim 77, and wherein Y is a ligand which may insert an olefin; M is a metal atom selected from Fe or Co, $NC^-$ is a non-coordinating anion and p+q is 2 or 3, matching the formal oxidation of said metal atom; L is a neutral Lewis donor molecule and n=0, 1, or 2.

88. The [bis-aryliminepyridine $MY_p \cdot L_n^+$][$NC^-$]$_q$ complex of claim 87 wherein $R_6$ and $R_{10}$ of the non-symmetrical ligand are each, independently, primary or secondary carbon atom group provided that $R_6$ and $R_{10}$ are not both a secondary carbon atom.

89. The [bis-aryliminepyridine $MY_p \cdot L_n^+$][$NC^-$]$_q$ complex of claim 87 wherein $R_{11}$ and $R_{15}$ of the bis-aryliminepyridine ligand are hydrogen.

90. The [bis-aryliminepyridine $MY_p \cdot L_n^+$][$NC^-$]$_q$ complex of claim 88 wherein $R_{11}$ and $R_{15}$ are hydrogen.

91. The [bis-aryliminepyridine $MY_p \cdot L_n^+$][$NC^-$]$_q$ complex of claim 87 wherein $R_6$ and $R_{10}$ of the non-symmetrical bis-aryliminepyridine ligand are each, independently, primary carbon atom group.

* * * * *